United States Patent [19]

Duska

[11] Patent Number: 4,506,676
[45] Date of Patent: Mar. 26, 1985

[54] RADIOGRAPHIC LOCALIZATION TECHNIQUE

[76] Inventor: Alois A. Duska, 2160 Via Olivera, Palos Verdes Estates, Calif. 90274

[21] Appl. No.: 416,489

[22] Filed: Sep. 10, 1982

[51] Int. Cl.³ .............................................. G03B 41/16
[52] U.S. Cl. .................................... 128/653; 378/162; 378/165
[58] Field of Search ................. 378/162, 165, 58, 163; 128/653

[56] References Cited

U.S. PATENT DOCUMENTS 3,917,952 11/1975 Jackson .............................. 378/165

FOREIGN PATENT DOCUMENTS 2459866 6/1976 Fed. Rep. of Germany ...... 378/165

OTHER PUBLICATIONS

X-Ray Identification Corporation, X-Rite Radio-Opaque Label Tape, 10/65, pp. 1 and 2.

Primary Examiner—Alfred E. Smith
Assistant Examiner—T. N. Grigsby
Attorney, Agent, or Firm—Poms, Smith, Lande & Rose

[57] ABSTRACT

To avoid problems in communication between the examining physician, the X-ray technician and the diagnosing radiologist, the present invention utilizes adhesive tape having radiopaque material incorporated into it. This tape is for use by the examining physician, to mark the exact location of concern. It will be visualized by the X-ray technician who shoots the film, and will then appear on the processed film to focus the attention of the radiologist to the area deserving closest attention.

4 Claims, 7 Drawing Figures

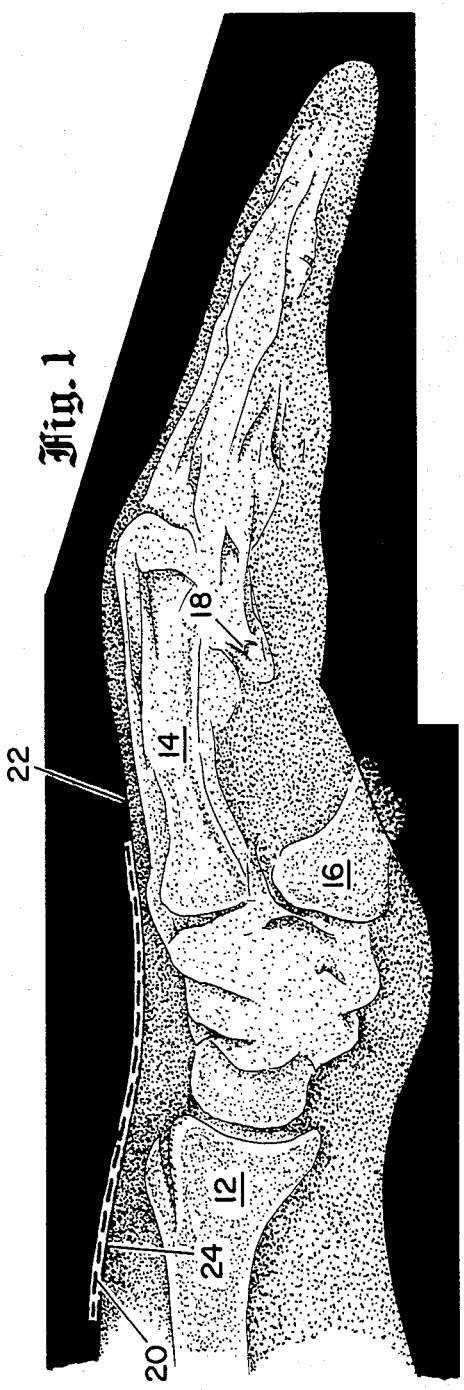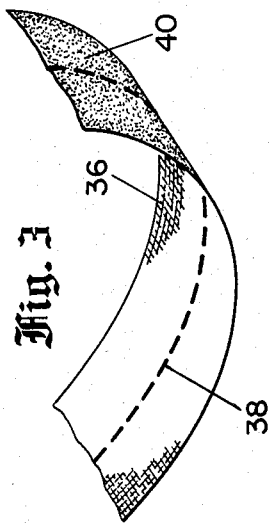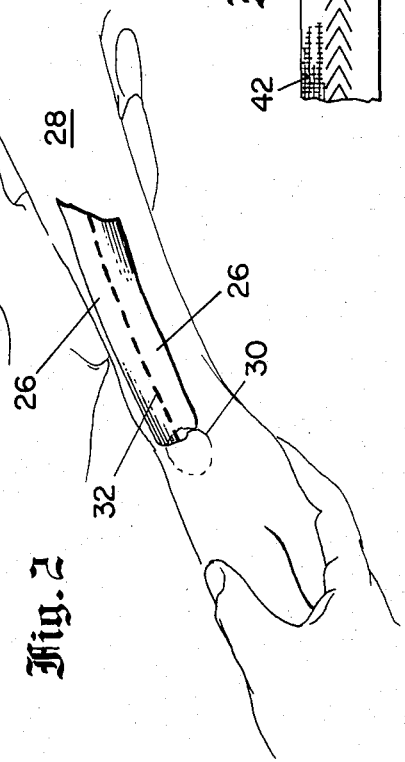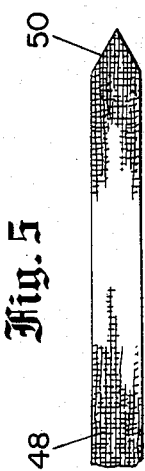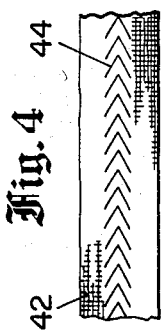

RADIOGRAPHIC LOCALIZATION TECHNIQUE

FIELD OF THE INVENTION

This invention relates to providing radiopaque marking indicators to improve X-ray diagnostic techniques.

BACKGROUND OF THE INVENTION

Each day countless numbers of X-rays are performed for medical diagnostic purposes. Unfortunately, as the practice of medicine has become increasingly specialized, these X-rays are interpreted by radiologists, who are also physicians, but who have not seen, nor examined the patient. The X-ray is normally taken by an X-ray technician and the X-rays are subsequently reviewed by the radiologist for interpretation and diagnosis. The radiologist normally relies on a cursory written comment from the examining physician on the need for the X-ray so that he will know where to focus his attention. These brief comments might characteristically be in a form such as "trauma to forearm" or "puncture wound to elbow". This method of inadequate communication between the examining physician and the radiologist has led to occasional errors in the reading of film, with subsequent medical consequences.

A recent study by David R. Milne, which appeared in the June 1982 issue of "Emergency Department News" on page 3, cites discordant interpretation of X-rays between radiologists and emergency physicians in 50 to 514 X-rays. In one day, for example, in a prominent medical center within Los Angeles County, two such fractures were initially missed by the radiologist. In each case the examining physician, knowing the exact point of tenderness by examination, was able to point out otherwise questionable lesions to the radiologist who with further views of the affected extremity, or with localized magnification, could identify the fracture. In these instances, no serious harm was done, but the patients had to be transferred back and forth between the doctor's office and the X-ray department until the exact nature of the injury was clarified.

Such incorrect radiographic interpretations have resulted in the following:

1. Missed lesions, such as fractures, with resultant inadequate treatment.

2. Excessive attempts at clarification of areas of questionable radiographic significance, but of no clinical significance, resulting in increased radiation, cost and discomfort to the patient.

3. Loss of time in critical situations, resulting from the need to repeat X-rays.

In order to locate tender areas, or entry sites in the case of puncture wounds, solid radiopaque members have sometimes been included in X-ray photographs. Thus, in some cases, markers are placed on the film itself to indicate entry sites for a puncture wound. In addition, in some rare instances, paper clips have been taped to a patient to indicate more clearly the location of an area requiring special attention. However, the placing of solid objects on the X-ray film itself leaves much to be desired, as the three dimensional positioning of the marker is not possible. In addition, in the rare instances where a solid element such as a paperclip has been taped to a patient, the change in orientation or the bending of the portion of the body for different X-ray positioning configurations, can result in movement of the solid member, or shifting of this member in its position, thereby defeating its purpose. Furthermore, since placing markers directly onto the film can only be done at the time of filming when only the X-ray technician who shoots the picture is present, and since this technician does not have the expertise to determine the area of concern, significant misrepresentation may occur.

Accordingly, a principal object of the present invention is to provide improved communication between the emergency physician, or the initial examining physician, the X-ray technician, and the radiologist, and to focus attention on the areas which have been determined by the examining physician to be tender or to otherwise deserve special attention. A more specific object of the present invention is to satisfy the radiologist's need for a more accurate radiographic localization of a patient's clinical complaint, thus hopefully minimizing discrepancies in the reading of X-ray film.

SUMMARY OF THE INVENTION

In accordance with the present invention, the emergency physician or initial exmining physician will mark a tender area on a patient with special adhesive tape which is marked with, or provided with, radiopaque material. The tape may either be a relatively thin piece of adhesive tape entirely covered with radiopaque material, or may be a broader adhesive tape with a row of radiopaque dots or arrow-like markings impregnated onto the tape. In either case, the adhesive tape is placed on the patient's skin extending toward the area deserving consideration up to but spaced from this area. The patient is then sent to the X-ray area, often in another part of the medical facility or hospital, located at a point remote from the place of initial examination. The X-ray technician, aided by the radiographic tape, is thereby assisted in taking the X-rays carefully of the precise area under consideration. Most important, of course, the radiologist has the benefit of the radiopaque indicators on the developed X-ray films showing the examining physician's indications of the area deserving close attention.

The invention as described hereinabove has the following advantages:

1. It is easily applied by the examining physician.

2. It remains secure during patient positioning and X-ray filming. In particular, it remains in a fixed position relative to the skin during repositioning for different X-ray views.

3. The radiopaque adhesive tape is flexible and supple to conform to irregular anatomical topography.

4. It has a radiopaque component which is readily apparent to the examining physician and the radiologist, but does not obscure the field of interest.

5. The radiopaque marking has a configuration that cannot possibly be mistaken for a foreign body.

6. The radiopaque adhesive tape is non-irritating to the patient, and is easily removable.

7. The radiopaque tape would be very low in cost relative to the improved interpretation and avoiding of the problems of improper diagnosis, as mentioned hereinabove.

In the implementation of the radiopaque tape, pressure sensitive medical tape, such as 3M's Micropore Tape, or Johnson and Johnson's Dermaclear Tape could be employed, and this type of tape could be impregnated or dotted with a suitable radiopaque paint or ink, for example barium sulfate pigment or very fine particles in a suitable carrier, which would evaporate to leave the desired radiopaque marking. A double layer adhesive tape could be used with short lengths of the rubber-like radiopaque threads, now used in medical sponges, could be used. A strip of one of these types of tape, with the radiopaque component incorporated into it, is secured along the skin surface, ending just before the point of anatomical interest. The X-ray films are shot, and when developed clearly indicate the exact area of concern within a given X-ray. The tape is of course easily removed from the patient and discarded. The radiologist, on viewing the films, recognizes the exact point of concern and is able to focus his attention on this affected area.

Other advantages include the possible identification of the entry point or the entry site for a foreign body. It is also particularly advantageous in the case of persons who have had a number of previous injuries, or arthritis, or other radiologically significant occurrences. Such persons, characteristically older persons, may have many points of X-ray interest on the films, possibly relating to old injuries, and the attention of the radiologist must be directed to the currently tender or critical areas.

Other objects, features and advantages of the present invention will become apparent from a consideration of the following detailed description and from the accompanying drawings.

BRIEF DESCRIPTION OF THE DRAWINGS

FIG. 1 represents an X-ray including the markings from a radiopaque tape, illustrating the principles of the present invention;

FIG. 2 shows the application of radiopaque tape to a patient by the examining physician;

FIGS. 3, 4 and 5 show various possible forms for the radiopaque tape;

DETAILED DESCRIPTION

Figure 6:
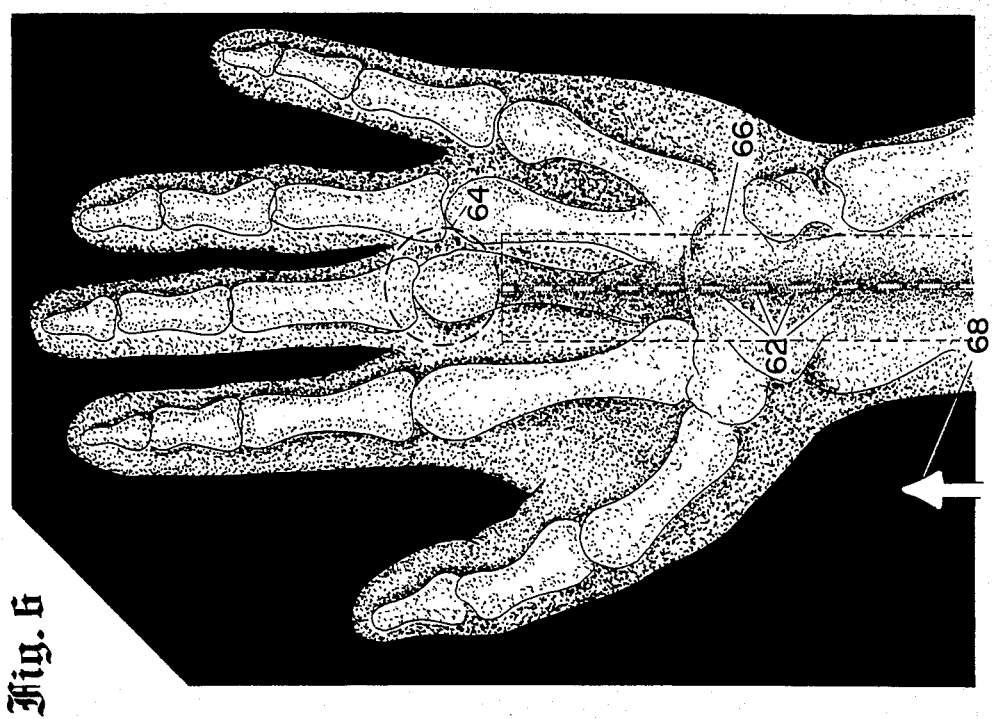
FIG. 6 is an A-P (anterior-posterior) view of the hand.

Referring now particularly to the drawings, FIG. 1 is an X-ray showing the hand of an 86 year old man. In FIG. 1 the forearm 12 is shown to the left, and metacarpal bones of the hand and thumb (14 and 16) are shown to the right. An old injury from a previous break is shown at reference numeral 18. The series of radiopaque dots 20 identifies the currently tender area 22, just beyond the end of this series of radiopaque dots 20. The position of the radiopaque tape is indicated by the circled area 24 adjacent the radiopaque dots 20; and the tape itself or the white area would of course not be visible on the developed X-ray film: only the radiopaque dots will appear as a series of white dots on the processed film.

FIG. 2 shows the application of the radiopaque tape 26 to the arm 28 of a patient (not the patient of the X-ray of FIG. 1). The tender wrist area 30 is identified by the radiopaque dots 32 in the tape 26 leading toward area 30.

Following the application of the tape 26, the patient whose arm is shown in FIG. 2 would be routed to the X-ray department, and after the usual wait, the X-ray technician would take the X-rays; and subsequently these X-rays would be analyzed by the radiologist and on occasion, even reviewed by the patient's physician. In the present instance, as noted above, the X-ray of FIG. 1 is not of the patient whose arm appears in FIG. 2, but the principles as outlined in these two figures are of course evident.

Now, referring to FIGS. 3, 4 and 5, these are representations of radiopaque tape which may be employed in the implementation of the method of the present invention. In FIG. 3, the tape 36 is provided with a series of radiopaque markings 38 forming a dashed line along the center of the tape 36. This may be accomplished through the use of an ink or a paint using barium sulfate, or other pigment or powdered or finely divided material known to be opaque to X-radiation, as the marking material and having no possible adverse medical effects. The adhesive tape 36 has the usual adhesive coating 40 on its lower surface for easy adhering to the skin of the patient. The tape 36 could, if desired, be a multiple layer tape, with the radiopaque material located between the two layers, but is preferably a single layer tape such as those made by Minnesota Mining & Manuacturing Co., or by Johnson & Johnson, as mentioned hereinabove. In FIG. 4, the tape 42 is provided with successive markings 44, which are carrot-shaped or in the configuration of arrows. In FIG. 5, a thinner radiopaque 48 is disclosed, and it is entirely coated with the radiopaque material. When such tape is employed, the end 50 may be pointed to more clearly direct attention to the desired area. In view of the greater obscuring of a portion of the anatomy by the tape 48, the style shown in FIG. 3 or that of FIG. 4 is to be preferred. More generally, it is important that the radiopaque tape be of such a configuration that it could not be mistaken for a foreign body such as a thin piece of metal or wire embedded in the anatomy of the patient.

Figure 7:
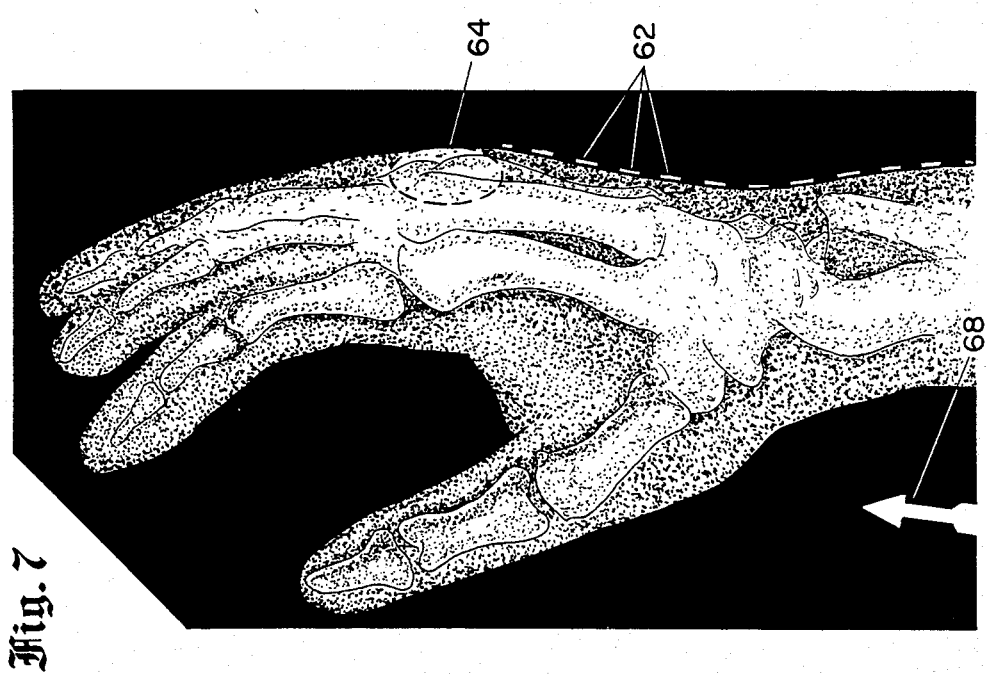
FIG. 7 is a lateral view of the hand shown in FIG. 6.

FIGS. 6 and 7 are a pair of normal X-ray views of the hand of a twenty-five year old man, illustrating the principles of the invention. FIG. 6 is a plan view or an anterior-posterior X-ray view of the hand; and FIG. 7 is a side or lateral view thereof. The series of radiopaque dashes 62 appear as white dashes on the developed X-ray film, and identifies the area of interest 64 at the head of the third metacarpal bone. The outlines 66 of the tape would of course not actually appear in the X-ray, but are shown in FIG. 6.

Also visible in FIG. 6 is an old-fashioned marker arrow which has sometimes been used by the X-ray technician to identify the supposed area of interest. In FIG. 6, the arrow is pointing to the side of the thumb to indicate that this is an "area of interest".

In FIG. 7, the dashed lines 62 from the radiopaque material indicate the area of interest 64, as in FIG. 6, thereby giving a three-dimensional localization. The marker 68 is again shown, and its deficiency in that it must be placed on the film, may be noted. In addition, the marker is, as noted above, not placed by the examining physician, but by the X-ray technician.

It is to be understood that the foregoing description and the accompanying drawings are merely illustrative of the principles of the invention. Other arrangements could be employed, for example, the tape could be made of paper, other radiopaque substanaces could be employed as the pigment for the ink or the paint which is employed to mark the tape, and small pieces, or a double thread of rubbery radiopaque material could be embedded in the tape, and it may of course be suitably colored blue or green, for example, to contrast with the color of the tape. As another alternative, small circular pieces of adhesive tape with X's or arrows, for example, of radiopaque material could also be employed to mark the area of interest. Also, the present technique using radiopaque tape is applicable to X-ray viewing systems using a viewing screen rather than X-ray films. Accordingly, it is to be understood that the present invention is not limited to that precisely as shown and described hereinabove.

What is claimed is:

1. A method for the medical examination and radiographic diagnosis of possible fractures or other medical problems, comprising the steps of:

initial examination of the patient;

securing flexible adhesive tape provided with a fine repetitive radiopaque pattern material to the patient's skin at the time of the initial examination, to locate critical areas such as tenderness, sensitivity or the entry point for foreign objects, said adhesive tape being of conventional type of medical tape formed of very flexible material provided with a series of evenly spaced unique radiopaque dots or other fine identifiable radiopaque indications to preclude possible confusion with foreign objects in the patient's body;

directing X-rays to the critical area of the patient as identified by the adhesive material and the fine radiopaque pattern and forming a visible image from the transmitted X-radiation; and viewing said visible image wherein the image of the fine radiopaque pattern indicates the areas to which primary attention should be directed;

whereby the original examining physician may identify the critical local area deserving primary attention by subsequent viewers of the X-ray images who may not have had the opportunity of examining the patient.

2. A method as defined in claim 1 wherein said securing step includes securing adhesive material having barium sulfate pigments as the radiopaque material.

3. A method for the medical examination, X-raying, and radiographic diagnosis of possible fractures or other medical problems, comprising the steps of:

initial examination of the patient, securing flexible adhesive tape provide with a fine radiopaque pattern to the patient's skin at the time of the initial examination, to locate critical areas such as tenderness, sensitivity or the entry point for foreign objects, said adhesive tape being of conventional type of medical tape formed of very flexible material provided with a series of evenly spaced unique radiopaque dots or other fine identifiable radiopaque indications to preclude possible confusion with foreign objects in the patient's body;

sending the patient to have X-rays taken, with the adhesive tape with fine radiopaque pattern being intact on the skin of the patient to direct the X-ray technician's attention to the localized area;

X-raying the localized area identified by the fine radiopaque patterned tape; and subsequently reviewing the resultant X-rays with the image of the fine radiopaque patterned tape indicating the area of the X-ray to be most clearly examined for diagnosis;

whereby the examining physician may permanently identify the critical local area deserving primary attention by the X-ray technician and the radiologist.

4. A method as defined in claim 3 wherein said securing step includes securing adhesive tape having barium sulfate pigments as the radiopaque material.

* * * * *